United States Patent
Sugrue et al.

(10) Patent No.: US 7,381,190 B2
(45) Date of Patent: Jun. 3, 2008

(54) INTRA-ABDOMINAL PRESSURE MONITORING URINARY CATHETER

(75) Inventors: Michael Sugrue, Homebush Sydney (AU); Zsolt Balogh, Lambton (AU)

(73) Assignee: Wolfe Tory Medical, Inc., Salt Lake City, UT (US)

( * ) Notice: Subject to any disclaimer, the term of this patent is extended or adjusted under 35 U.S.C. 154(b) by 66 days.

(21) Appl. No.: 11/219,316

(22) Filed: Sep. 1, 2005

(65) Prior Publication Data

US 2006/0079804 A1 Apr. 13, 2006

Related U.S. Application Data

(63) Continuation of application No. PCT/AU2004/000282, filed on Mar. 8, 2004.

(30) Foreign Application Priority Data

Mar. 10, 2003 (AU) .............. 2003901057

(51) Int. Cl.
*A61B 5/00* (2006.01)
(52) U.S. Cl. .................................. 600/561
(58) Field of Classification Search ........ 600/561, 600/587, 573, 574, 581, 591, 593, 477, 476, 600/560, 300; 604/317–328, 191–194, 100, 604/28; 73/700, 714
See application file for complete search history.

(56) References Cited

U.S. PATENT DOCUMENTS

| | | | |
|---|---|---|---|
| 1,666,332 A | 4/1928 | Hirsch | |
| 1,712,848 A | 5/1929 | Rose | |
| 3,620,255 A | 11/1971 | Stillman | |
| 3,794,043 A | 2/1974 | McGinnis | |
| 4,210,173 A | 7/1980 | Choksi et al. | |
| 4,217,911 A | 8/1980 | Layton | |
| 4,301,811 A | 11/1981 | Layton | |
| 4,538,621 A * | 9/1985 | Jarczyn | 600/561 |
| 4,966,161 A | 10/1990 | Wallace et al. | |
| 5,385,563 A | 1/1995 | Gross | |

(Continued)

FOREIGN PATENT DOCUMENTS

EP 0 258 690 8/1987

(Continued)

OTHER PUBLICATIONS

PCT International Search Report, PCT/AU2004/000282, dated Apr. 28, 2004.

(Continued)

*Primary Examiner*—Max Hindenburg
*Assistant Examiner*—Fangemonique Smith
(74) *Attorney, Agent, or Firm*—TraskBritt

(57) ABSTRACT

A urinary catheter and method of its use for measuring the internal pressure of a human or other mammal. The catheter includes three lumens, or channels. The first lumen is dedicated to draining urine, the second lumen is dedicated to a retention balloon, and the third lumen is available for connection to a pressure transducer. In use, the catheter is installed in a patient, the third lumen is filled with a pressure transmitting medium, connected to a pressure sensor, and the patient's intra-abdominal pressure is monitored without interruption of the urine flow.

6 Claims, 2 Drawing Sheets

U.S. PATENT DOCUMENTS

| | | | |
|---|---|---|---|
| 5,433,216 A * | 7/1995 | Sugrue et al. | 600/591 |
| 5,713,850 A | 2/1998 | Heilmann et al. | |
| 5,865,764 A | 2/1999 | Moorhead | |
| 5,916,153 A * | 6/1999 | Rhea, Jr. | 600/310 |
| 6,102,888 A * | 8/2000 | Walker | 604/28 |
| 6,334,064 B1 * | 12/2001 | Fiddian-Green | 600/311 |
| 6,434,418 B1 * | 8/2002 | Neal et al. | 600/511 |
| 6,447,462 B1 * | 9/2002 | Wallace et al. | 600/561 |
| 6,494,208 B1 | 12/2002 | Morejon | |
| 6,503,208 B1 | 1/2003 | Skovlund | |
| 7,112,177 B2 | 9/2006 | Christensen et al. | |
| 2002/0065472 A1 | 5/2002 | Brockway et al. | |
| 2002/0082610 A1 | 6/2002 | Cioanta et al. | |

FOREIGN PATENT DOCUMENTS

WO    WO 2004/080519 A1    9/2004

OTHER PUBLICATIONS

PCT Written Opinion, PCT/AU2004/000282, dated Apr. 28, 2004.

Fusco et al., "Estimation of Intra-abdominal Pressure by Bladder Pressure Measurement: Validity and Methodology," The Journal of Trauma® Injury, Infection, and Critical Care, Feb. 2001, pp. 297-302, vol. 50, No. 2.

Kirkpatrick et al., "Is Clinical Examination an Accurate Indicator of Raised Intra-abdominal Pressure in Critically Injured Patients?" CJS, Jun. 2000, pp. 207-211, vol. 43, No. 3.

Lozen et al., "Intraabdominal Hypertension and Abdominal Compartment Syndrome in Trauma: Pathophysiology and Interventions," AACN Clinical Issues: Advanced Practice in Acute Critical Care, Feb. 1999, pp. 104-112, vol. 10, No. 1.

Malbrain et al., "Abdominal pressure in the critically ill: measurement and clinical relevance," Intensive Care Med, 1999, pp. 1453-1458, vol. 25.

Sugrue et al., "Intra-abdominal pressure: time for clinical practice guidelines?" Intensive Care Med, 2002, pp. 389-391, vol. 28.

PCT International Preliminary Report on Patentability, PCT/US2005/042406 issued Jun. 5, 2007.

* cited by examiner

INTRA-ABDOMINAL PRESSURE MONITORING URINARY CATHETER

CROSS-REFERENCE TO RELATED APPLICATION

This application is a continuation of PCT International Patent Application No. PCT/AU2004/000282, filed on Mar. 8, 2004, designating the United States of America, and published, in English, as PCT International Publication No. WO 2004/080519 A1 on Sep. 24, 2004, the contents of the entirety of which is incorporated by this reference.

BACKGROUND OF THE INVENTION

The following statement is a full description of the invention and includes the best method of performing it.

This invention relates medical diagnostic equipment and methods and is particularly concerned measuring intra-abdominal pressure using direct or remote sensing of pressure within the organ in particular Intra-abdominal pressure and related pressure within adjacent organs.

Until the advent of recent publication in relating to renal failure and complication of pressure after surgery few considered intra-abdominal pressure measurement to be important. It is now recognized as an important part of post-operative care.

Currently intra-abdominal pressure is measured using a urinary catheter requiring insertion of an extra T-piece or a needle directly into the urinary catheter to allow the pressure to be measured using a transducer or a manometer.

A wide variety of innovative techniques have been used to measure IAP in nearly every part of the abdominal cavity, including the rectum, stomach, urinary bladder, uterus, liver, inferior vena cava, and free within the intra-peritoneal cavity.

Rectal pressure measurement was experimentally popular in the early part of this century, using a Miller Abbott tube. It would appear generally it is a simple but slightly unreliable technique.

McCarthy in 1982 in a study of 12 patients undergoing urodynamic evaluation and laparoscopic tubal ligation found that there was a good correlation between intra-abdominal and rectal pressures. He expressed concern that reliability of this technique required the catheter to remain 10 cm above the anal verge otherwise the values were greater than the abdominal values. Presumably this was due to the spontaneous activity of the rectal sphincters. Shafik used rectal pressure in many of his experiments in humans on rectal detrusor muscle activity. He used a urinary catheter with an outer diameter of 1.2 mm and found that there was good visual correlation between intravesical and rectal pressures.

Intra-gastric measurement was used in the early part of this century with a Hamilton manometer, which afforded the simplest and most reliable technique at the time.

Simple techniques using nasogastric tubes to measure IAP have been used by Cullen, Fietsam and Collee. Concern has been expressed about simple perfusion techniques using a nasogastric tube, and Lacey in an animal study found that the use of gastric pressure measurement through an irrigational portal of the nasogastric tube is not reproducible. Collee, from London, used an unperfused nasogastric tube to obtain 141 paired measurements in 26 general surgery patients in ICU. He found using appropriate statistical modeling, that gastric pressure may be 2.5 cm of water above or below intra-vesical pressure.

The intra gastric route has two specific advantages. It can be used when there has been trauma to the bladder or where the patient does not have a urinary catheter in place. Gastric pressures are also very useful when there is a tense pelvic haematoma following pelvic trauma, as vesical pressures in this situation may not reflect general IAPs.

Direct cannulation of the peritoneal cavity had been used experimentally, but it is not as accurate as the intravesical technique and is invasive.

Motew used a Verres needle to measure IAP in an experiment on 12 women undergoing tubal ligation. The use of a Verres needle to measure IAP may not be accurate during flow states. It is also dependent on the degree of muscle relaxation required for the laparoscopy. Obeid and colleagues, from Detroit, reported in 1995 a comparison of IAP measurement using four techniques in 28 patients. These included an intra-gastric route via a simple NG, a laparoscopic insufflator rectal pressure via a modified oesophageal stethoscope and a standard intra-vesical method with a urinary catheter. Obeid found that with a standard 6 mmHg rise in IAP, as measured by the insufflator, this was best correlated with the intravesical measurements, with a rise of 5.7 mmHg ($\pm$9.8). The gastric and rectal pressures were less reliable with the following changes recorded, $-0.7\pm9.8$ mmHg and $3.3\pm8.8$ mmHg respectively. He found the rectal and gastric pressures were more position dependent and less reliable than the intravesical approach. The specific limitation of the laparoscopic technique in Obeid's study is the lack of validation of the Stryker endoscopy high flow insufflator, which was used as the gold standard to compare with the other methods. In clinical practice pressures measured with such laparoscopic insufflators may fluctuate widely during surgery. This can be related to the depth of anaesthesia and port mechanics including blockage with blood or other products.

Because of the fluid dynamics in the abdominal cavity, IAP can also be measured through a central venous line if its tip is in the inferior vena cava. This has been utilized by a number of researchers. Lacey in a study of rabbits, comparing different sites of IAP measurement found an excellent correlation between IVC pressures and vesical IAP readings. It should be remembered that these experiments were performed in rabbits, under general anaesthesia.

In addition Lacey found that there was poor correlation between superior vena cava, rectus abdominus and rectal pressure.

The gold standard for IAP measurement has been the intravesical technique. Unfortunately Kron did not test the reliability of his technique and validation of the intravesical technique was undertaken and published by Iberti and colleagues at Mount Sinai medical centre in 1989. In a study of post-operative patients with closed intra-abdominal drains they compared urinary catheter measurements with those recorded from the abdominal drains. They used the pubis as the zero point which may give rise to slightly reduced as it lies above the mid point of the abdominal cavity.

Iberti's investigations revealed a good correlation between intra-abdominal and intra-vesical pressure. In addition he found that there was little effect of positive end expiratory pressure (PEEP) on IAP. I have modified the technique slightly and the technique used in this project is according to the protocol below;

Other techniques, including installation of saline into the bladder and holding the catheter in the air have also been described. They are cumbersome, do not provide on-line monitoring or are time consuming.

Previously the direct on-line monitoring of urinary catheters has not been reported as a measure of intra-abdominal pressure. Urinary catheters usually contain two lumens, one for the balloon and one for the urine flow.

For patients with haematuria, triple lumen catheters have been used for years. They allow irrigation through the third lumen. They have not been used or reported to measure intra-abdominal pressure.

DETAILED DESCRIPTION OF THE ILLUSTRATED EMBODIMENT

The present problems with intra-abdominal pressure measurement are overcome by the present invention, which provides direct access to the triple lumen urinary catheter's third lumen, allowing direct transducing of intra-abdominal pressure directly without interruption of urine flow.

Figure 1:
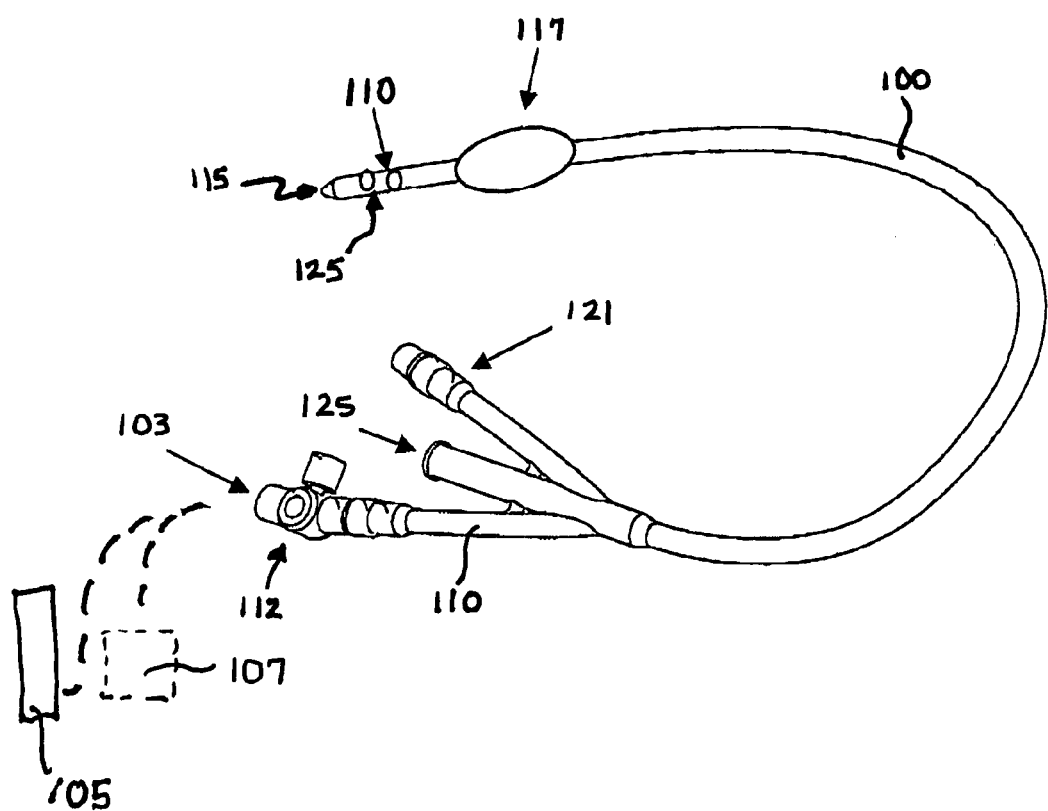
FIG. 1: Components of the intra-abdominal pressure measuring urinary catheter.

In one embodiment of the invention, the urinary catheter 100 contains a Luer lock 103, allowing direct connection to a transducing manometer 105 or remote sensor 107 (FIG. 1).

Figure 2:
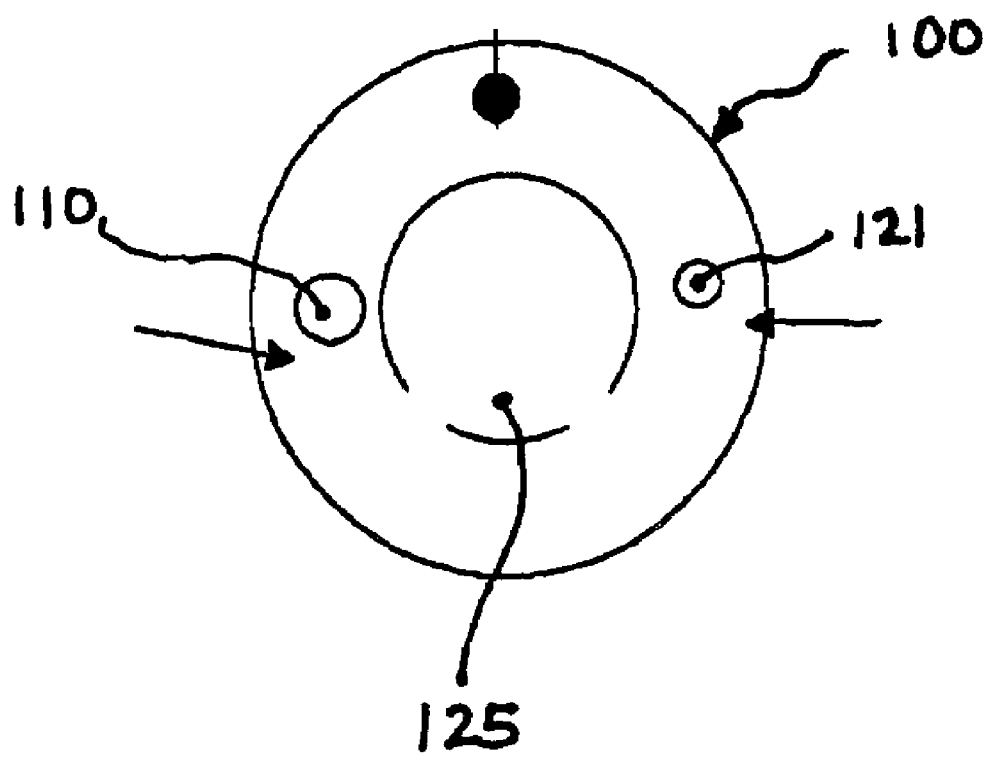
FIG. 2: Cross section of intra-abdominal pressure measuring urinary catheter.

The line 110 is irrigated with a liquid and connected to a pressure transducer 105, 107 for on-line pressure measurement. A cross section of the tube 100 is shown in FIG. 2.

In yet another aspect or embodiment, the device uses a T-piece 112 attached to the pressure transducing channel 110 to allow remote pressure reading. Optionally, when a temperature sending means is required, this may be added to the catheter 100. In an embodiment of the present invention, a pressure transmitting channel 110 which is filled with a medium, either air or liquid, can be attached to a Luer lock 103 with a three way tap 112 allowing irrigation or perfusion of that channel. The change in pressure at the end 115 of the catheter is thereby transmitted and communicated to the pressure transducing medium.

In an embodiment of the invention, the pressure transmission can be connected to a manometer 105 or liquid column at the patient bedside.

The pressure measuring urinary catheter 100 may be left in the patient for unspecified times and measurement recorded continuously or at intervals. The catheter may be made of a material meeting international standards for medical use, silicone, PVC, latex or other material.

The urinary catheter 100 is inserted through the urethra, under standard sterile conditions, with use of the retention balloon 117 insufflated with saline through channel 121. Urine drains through urine channel 125.

The invention claimed is:

1. A method for direct, on-line monitoring of the intra-abdominal pressure of a medical patient, the method comprising:
   a) installing into said medical patient an apparatus comprising:
   an elongate urinary catheter comprising:
      a first lumen adapted for fluid communication with a retention balloon carried at a distal end of the elongate urinary catheter,
      a second lumen adapted for uninterrupted draining of urine from the medical patient's bladder, and
      a third lumen adapted for open fluid communication through proximal and distal ends of the elongate urinary catheter to permit instilling of a pressure transmitting medium into the medical patient's bladder allowing drainage of the pressure transmitting medium through the second lumen and to permit the transmission of change of the pressure through the third lumen via the pressure transmitting medium, without interrupting urine flow from the elongate urinary catheter;
   a pressure sensor for measuring the pressure of the pressure transmitting medium; and
   removable coupling structure comprising an adapter that can be affixed to a proximal end of the third lumen and operable to place the pressure sensor into fluid communication with the pressure transmitting medium;
   b) irrigating said third lumen thereof with a pressure transmitting medium; and
   c) monitoring the pressure of said pressure transmitting medium without interruption of urine discharge from said patient so as to determine the intra-abdominal pressure of the medical patient with said apparatus.

2. The method according to claim 1, further comprising the steps of
   installing coupling structure into a proximal end of said third lumen; and
   operating said coupling structure to place said third lumen and a pressure sensor into fluid communication.

3. The method according to claim 2 wherein:
said coupling structure comprises a Luer-lock fitting.

4. The method according to claim 2 wherein:
said coupling structure comprises a T-piece.

5. The method according to claim 2, wherein:
said coupling structure comprises a 3-way tap.

6. A method for measuring the intra-abdominal pressure of a medical patient, the method comprising the steps of:
   placing an apparatus comprising:
   an elongate urinary catheter comprising:
      a first lumen adapted for fluid communication with a retention balloon carried at a distal end of the elongate urinary catheter;
      a second lumen adapted for uninterrupted draining of urine from the medical patient's bladder; and
      a third lumen adapted for open fluid communication through proximal and distal ends of the elongate urinary catheter to permit instilling of a pressure transmitting medium into the medical patient's bladder allowing drainage of the pressure transmitting medium through the second lumen and to permit the transmission of change of the pressure through the third lumen via the pressure transmitting medium, without interrupting urine flow from the elongate urinary catheter;
   a pressure sensor for measuring the pressure of the pressure transmitting medium; and
   removable coupling structure comprising an adapter that can be affixed to a proximal end of the third lumen and operable to place the pressure sensor into fluid communication with the pressure transmitting medium and into fluid communication with a bladder of said medical patient;
   connecting a pressure sensor to said apparatus's urinary catheter effective to permit said sensor to measure a pressure of fluid in said bladder; and
   measuring said pressure while permitting urine discharge from said medical patient's bladder.

* * * * *